US012582826B2

(12) United States Patent     (10) Patent No.:   US 12,582,826 B2

Huegerich et al.     (45) Date of Patent:    Mar. 24, 2026

(54) INTRA-BODY NETWORK SYSTEM

(71) Applicant: BIOTRONIK SE & Co. KG, Berlin (DE)

(72) Inventors: Burkhard Huegerich, Portland, OR (US); Andrew B. Kibler, Lake Oswego, OR (US); Min Qu, Portland, OR (US); Habib Homayoun, Beaverton, OR (US)

(73) Assignee: Biotronik SE & Co. KG, Berlin (DE)

( * ) Notice: Subject to any disclaimer, the term of this patent is extended or adjusted under 35 U.S.C. 154(b) by 227 days.

(21) Appl. No.: 18/264,826

(22) PCT Filed: Apr. 26, 2022

(86) PCT No.: PCT/EP2022/060956
§ 371 (c)(1),
(2) Date: Aug. 9, 2023

(87) PCT Pub. No.: WO2022/233633
PCT Pub. Date: Nov. 10, 2022

(65) Prior Publication Data

US 2024/0050756 A1    Feb. 15, 2024

Related U.S. Application Data

(60) Provisional application No. 63/184,493, filed on May 5, 2021.

(30) Foreign Application Priority Data

Jun. 7, 2021    (EP) ..................................... 21177959

(51) Int. Cl.
*A61N 1/372*      (2006.01)
*A61N 1/365*      (2006.01)
(Continued)

(52) U.S. Cl.
CPC ..... *A61N 1/37276* (2013.01); *A61N 1/36564* (2013.01); *A61N 1/37229* (2013.01);
(Continued)

(58) Field of Classification Search
None
See application file for complete search history.

(56) References Cited

U.S. PATENT DOCUMENTS 6,141,588 A    10/2000   Cox et al.
2006/0241724 A1*   10/2006   Dublin ............... A61N 1/37223
                                         607/32
(Continued)

FOREIGN PATENT DOCUMENTS

EP       2327609 B1    1/2016
JP       H10513368 A   12/1998
(Continued)

OTHER PUBLICATIONS

International Search Report (PCT/ISA/210) and Written Opinion (PCT/ISA/237) mailed on Jul. 11, 2022, by the European Patent Office as the International Searching Authority for International Application No. PCT/EP2022/060956. (14 pages).
(Continued)

*Primary Examiner* — Mallika D Fairchild
(74) *Attorney, Agent, or Firm* — Buchanan Ingersoll & Rooney PC

(57)             ABSTRACT

An intra-body network system, comprises a first implantable medical device comprising a first communication circuitry and a second implantable medical device comprising a second communication circuitry. The first and second communication circuitries are configured to establish, in an implanted state of the first and second implantable medical devices, a communication for transmitting a communication signal from the first implantable medical device to the
(Continued)

second implantable medical device and from the second implantable medical device to the first implantable medical device. The first and/or second implantable medical devices comprises an antenna arrangement configured to transmit and/or receive a communication signal in a first configuration state using a first directive radiation characteristic, in a second configuration state using a second directive radiation characteristic different from the first directive radiation characteristic and a third configuration state using a third directive radiation characteristic different from the first and second directive radiation characteristics.

14 Claims, 4 Drawing Sheets

(51) Int. Cl.
    *A61N 1/375*     (2006.01)
    *A61N 1/39*     (2006.01)
    *H04L 67/12*     (2022.01)

(52) U.S. Cl.
    CPC ....... *A61N 1/37288* (2013.01); *A61N 1/3756* (2013.01); *A61N 1/39622* (2017.08); *H04L 67/12* (2013.01)

(56) References Cited

U.S. PATENT DOCUMENTS

| | | | |
|---|---|---|---|
| 2007/0239229 A1* | 10/2007 | Masoud | A61B 5/0031 |
| | | | 607/60 |
| 2010/0022836 A1 | 1/2010 | Colliou et al. | |
| 2011/0046698 A1* | 2/2011 | Kivi | H04W 76/19 |
| | | | 607/60 |
| 2011/0087114 A1 | 4/2011 | Moulder | |
| 2013/0194106 A1 | 8/2013 | Lee et al. | |
| 2013/0268028 A1* | 10/2013 | Trier | A61N 1/37223 |
| | | | 607/60 |
| 2015/0202450 A1 | 7/2015 | Trier et al. | |
| 2016/0250483 A1 | 9/2016 | Klimovitch et al. | |
| 2019/0030346 A1* | 1/2019 | Li | A61N 1/3702 |
| 2019/0192863 A1* | 6/2019 | Koop | A61N 1/37516 |

FOREIGN PATENT DOCUMENTS

| | | |
|---|---|---|
| JP | 2017501839 A | 1/2017 |
| JP | 2018509986 A | 4/2018 |
| JP | 2021041168 A | 3/2021 |

OTHER PUBLICATIONS

Office Action for Japanese Patent Application No. 2023-543010 dated Dec. 12, 2025 (with English Translation).

* cited by examiner

INTRA-BODY NETWORK SYSTEM

CROSS-REFERENCE TO RELATED APPLICATIONS

This application is the United States National Phase under 35 U.S.C. § 371 of PCT International Patent Application No. PCT/EP2022/060956, filed on Apr. 26, 2022, which claims the benefit of European Patent Application No. 21177959.0, filed on Jun. 7, 2021 and U.S. Provisional Patent Application No. 63/184,493, filed on May 5, 2021, the disclosures of which are hereby incorporated by reference herein in their entireties.

TECHNICAL FIELD

The instant invention generally relates to an intra-body network system and a method for operating an intra-body network system.

BACKGROUND

An intra-body network system of this kind generally comprises a first implantable medical device and a second implantable medical device. Within the intra-body network system, the implantable medical devices shall communicate with each other, in order to for example exchange information relating for example to sensed cardiac signals or the like, or to adjust operation of multiple implantable medical devices, e.g., to trigger an action of one implantable medical device by a sense signal of another implantable medical device.

An implantable medical device of this kind may for example be a pacemaker, an implantable cardioverter defibrillator, a sensor device such as a bio-sensor for measuring a blood pressure, or a recording device such as a loop recorder to be subcutaneously implanted in a patient.

An implantable pacemaker may for example be subcutaneously implanted in a patient and may comprise leads carrying electrodes and extending from a generator unit of the pace-maker device into the patient's heart for example to provide a pacing action in the right ventricle of the heart. Alternatively, an implantable pacemaker device may be designed as a leadless pacemaker not comprising leads, but being directly implanted into the patient's heart, for example in the right ventricle in order to provide for a pacing action.

A cardioverter defibrillator may serve for monitoring and treating potentially life-threatening arrhythmias in a patient's heart, wherein a cardioverter defibrillator of this kind may for example be implanted subcutaneously and may comprise leads extending into the patient's heart in order to record signals and to inject stimulation energy into the patient's heart for example to provide an electric shock (defibrillation).

Sensor devices, such as pressure sensors, flow sensors, temperature sensors or the like, may for example be implanted into a blood vessel, such as a vein, in order to provide for a monitoring of relevant parameters in the context of providing a therapy.

A loop recorder is for example subcutaneously implanted and serves to continuously record information for example about cardiac activity, such as an ECG. A loop recorder may continuously loop its memory and may store particular portions of signals, such that recorded signals may be communicated to an external device for analyzing the signals and for providing a diagnosis.

There is a desire that medical devices implanted in a patient may communicate with each other in order to allow the medical devices to interact. For example, signals sensed by a pacemaker device or an implanted sensor device may be transmitted to a loop recorder such that the loop recorder may record such signals. In addition, a pacemaker device may receive signals from a sensor device implanted remotely from the pacemaker device in order to take sensing signals of the sensor device into account for controlling a pacing action in the patient's heart.

For establishing a communication, approaches exist to create an intra-body network (IBN) linking implanted medical devices with each other such that signals may be exchanged in between the implanted medical devices.

For example, European Patent No. 2 327 609 B1 describes an acoustic communication link in between implanted medical devices for exchanging information in between the implanted medical devices. The acoustic communication link is established to permit wireless communication between the implanted medical devices, wherein transmission parameters may be adapted, such as a sensitivity and a carrier frequency, in order to improve an existing communication link.

A wireless communication in between implanted medical devices may generally involve acoustic, radio frequency (RF), modulated electric fields or magnetic signals. Generally, herein, signals are transmit-ted using a particular carrier frequency, wherein a transmission may be initiated by one implantable medical device for reception by another medical device. If one medical device transmits a signal, it herein must be ensured that the other medical device is able to receive said signal. As implantable medical devices generally are small in size and hence may comprise only a simplified processing circuitry, it may be the case that an implantable medical device may not be able to comprise extensive circuitry for establishing a communication, wherein signals should be of low power in order to not overly place a load on the device's energy storage.

U.S. Publication No. 2010/0022836 A1 discloses multi-directional transmitters for in-body devices, such as implantable and indigestible devices. The multiple multidirectional transmitters shall be enabled to transmit an identifying signal in at least two different directions.

U.S. Publication No. 2011/0087114 A1 discloses an implantable medical device which is capable of sensing and determining its orientation, and of determining whether the implantable medical device has been displaced over time away from its original or optimal position.

U.S. Publication No. 2016/0250483 A1 discloses an implantable medical device which is configured to be implanted within a patient, the implantable medical device including a controller configured to adjust a communication frequency, a housing formed of an electrically common material, and an insulating cover coupled to the housing.

The present disclosure is directed toward overcoming one or more of the above-mentioned problems, though not necessarily limited to embodiments that do.

SUMMARY

It is an object of the instant invention to provide an intra-body network system and a method for operating an intra-body network system which allow for a reliable, yet power efficient communication in between implantable medical devices.

In one aspect, an intra-body network system comprises: a first implantable medical device comprising a first communication circuitry; and a second implantable medical device comprising a second communication circuitry; wherein the first communication circuitry and the second communication circuitry are configured to establish, in an implanted state of the first implantable medical device and the second implantable medical device, a communication for transmitting a communication signal from at least one of the first implantable medical device to the second implantable medical device and the second implantable medical device to the first implantable medical device; wherein at least one of the first implantable medical device and the second implantable medical device comprises an antenna arrangement configured to at least one of transmit and receive a communication signal in a first configuration state using a first directive radiation characteristic and in a second configuration state using a second directive radiation characteristic different from the first the director of radiation characteristic.

Accordingly, at least one of the first implantable medical device and the second implantable medical device comprises an antenna arrangement which is capable of transmitting and/or receiving communication signals along different directions. For this, the antenna arrangement uses, in a first configuration state, a first directive radiation characteristic and, in a second configuration state, a second directive radiation characteristic. A directive radiation characteristic in this context is to be understood as a radiation pattern which for an antenna arrangement, such as an electromagnetic antenna arrangement, is generally three-dimensional, but is directional in that signals are transmitted and/or received preferentially along a defined direction or within a defined plane. Hence, within a defined direction or a defined plane the antenna arrangement transmits signals with a maximum amplitude and comprises, upon reception, a maximum sensitivity.

Because the antenna arrangement may be switched between the first configuration state and the second configuration state, different directive radiation characteristics may be used. Hence, by using the first configuration state or the second configuration state the antenna arrangement may transmit and/or receive signals with a particular, associated directional characteristic. By choosing a suitable configuration state for communicating with a particular, other implantable medical device, a reliable communication may be established, in that such configuration state may be chosen which transmits signals or receive signals with a particular directional characteristic suitable for communication with the other implantable medical device.

The antenna arrangement is configured to communicate using at least the first configuration state and the second configuration state. However, also more than two configuration states may be available (e.g., a third configuration state), such that the antenna arrangement may also use another, further configuration state for communication with an implantable medical device.

The intra-body network system comprises at least two implantable medical devices. However, also more than two implantable medical devices may be used within the intra-body network system. For a communication in between a particular pair of implanted medical devices, a particular configuration state of an antenna arrangement of at least one of the implantable medical devices may be used.

Within a particular implantable medical device, different configuration states of an antenna arrangement may be used for communicating with different implantable medical devices, such that the implantable medical device may choose from the available communication states in order to communicate with a particular one of the multiple other implantable medical devices.

Within the intra-body network system, (only) one or some of the implantable medical devices may comprise an antenna arrangement having different configurations states, wherein another implantable medical device does not comprise such antenna arrangement. However, in a beneficial embodiment, each implantable medical device of the intra-body network comprises an antenna arrangement having multiple configurations states for communicating with other implantable medical devices.

Additionally or alternatively, at least one of the first implantable medical device and the second implantable medical device may comprise an antenna arrangement configured to at least one of transmit and receive a communication signal in a first configuration state using a first directive radiation characteristic, in a second configuration state using a second directive radiation characteristic different from the first directive radiation characteristic and a third configuration state using a third directive radiation characteristic different from the first directive radiation characteristic and the second directive radiation characteristic.

In one embodiment, the antenna arrangement is configured to at least one of transmit and receive a communication signal in the first configuration state predominantly along a first communication plane and in the second configuration state predominantly along a second communication plane. The communication planes differ from each other and may be arranged for example at a perpendicular angle or at another, skewed angle with respect to each other.

If more than two configuration states (e.g., three communication states) exist, more than two communication planes (e.g., three communication planes) may be associated with the different configuration states, the communication planes differing from each other, a particular communication plane being associated with a particular one of the configuration states of the antenna arrangement.

Thus, in one embodiment, the antenna arrangement is configured to at least one of transmit and receive a communication signal in said first configuration state predominantly along a first communication plane, in said second configuration state predominantly along a second communication plane and in said third configuration state predominantly along a third communication plane.

In one embodiment, the antenna arrangement comprises at least three antenna elements, wherein the antenna arrangement is configured to use a first set of the at least three antenna elements in the first configuration state and a second set of the at least three antenna elements in the second configuration state. The antenna arrangement may for example comprise (much) more than three antenna elements, for example five, six, ten or more or even twenty or more antenna elements. By choosing a particular set of antenna elements for communication, a particular directive radiation characteristic may be established for communicating (i.e., at least one of transmitting and/or receiving) signals with another implantable medical device within the intra-body network system.

Additionally or alternatively, the antenna arrangement is configured to use a first set of the at least three antenna elements in the first configuration state, and a second set of the at least three antenna elements in the second configuration state and a third set of the at least three antenna elements in the third configuration state.

In one embodiment, at least one of the at least three antenna elements is formed by an electrode for emitting or receiving (predominantly) electrical signals, in particular RF or modulated electric field signals.

Such electrode may for example by a dedicated electrode which solely serves for establishing a communication. In another embodiment, the electrode may be a sensing electrode for sensing intra-cardiac signals, such that the sensing electrode is used both for sensing signals and for communicating with another implantable medical device within the intra-body network system.

In one embodiment, at least one of the at least three antenna elements is formed by a coil for emitting or receiving (predominantly) magnetic signals. Hence, communication with another implantable medical device may be established by using magnetic signals.

In one embodiment, the implantable medical device having the antenna arrangement comprises a housing, wherein at least one of the at least three antenna elements is placed on the housing. The antenna element may be a dedicated antenna element serving for establishing a communication. The antenna element placed on the housing however may also serve an additional function for example for sensing cardiac signals, such as it is the case for a sensing electrode for sensing intra-cardiac electrical signals.

Multiple antenna elements herein may be placed on different locations on the housing. By choosing a set of antenna elements, thus, different directive radiation characteristics may be established, as determined by the set of antenna elements and their physical location on the implantable medical device.

In one embodiment, the implantable medical device having the antenna arrangement comprises a fixation arrangement comprising at least one fixation element. A fixation element of this kind may for example have the shape of a bendable tine, for example made of a shape memory alloy material, such as nitinol, which may be brought into engagement with tissue in order to establish a fixation of the implantable medical device to tissue, for example intra-cardiac tissue. In another embodiment, a fixation element may for example have the shape of a screw in order to fix the implantable medical device to tissue, for example intra-cardiac tissue.

Herein, at least one of the at least three antenna elements may be placed on the at least one fixation element, such as a tine or a screw. Herein, the fixation element, which for example may be fabricated from an electrically conductive material, as a whole may form the antenna element. In another embodiment, one or multiple antenna elements (e.g., in the shape of electrodes) may be placed on the fixation element, the antenna elements being electrically insulated from one another such that they may be excited substantially independent of one another.

In one embodiment, at least one of the first communication circuitry and the second communication circuitry is configured, in an initialization phase, to at least one of transmit and receive a communication signal using the first configuration state and the second configuration state of the antenna arrangement in order to select a configuration state out of the first configuration state and the second configuration state and, in an operational state, to use the selected configuration state for communication.

In one embodiment, at least one of the first communication circuitry and the second communication circuitry is configured, in the initialization phase, to at least one of transmit and receive a communication signal by sequentially using the first configuration state, the second configuration state and the third configuration state of the antenna arrangement in order to select a configuration state out of the first configuration state, the second configuration state and the third configuration state.

Hence, in an initialization phase, for example following implantation of the implantable medical devices of the intra-body network within the patient, an initial communication in between the implantable medical devices is established. For this, an implantable medical device may scan through available configuration states in order to establish which configuration state is best suitable for communicating with another implantable medical device. Once the best configuration state is identified, during actual operation this selected configuration state may be used for communicating with a particular other implantable medical device, wherein different configuration states may be selected for communication with different implantable medical devices such that a particular configuration state may be chosen as best suitable for communication with a particular other implantable medical device.

The scan through the different available (e.g., two or three) configuration states may in particular take place sequentially, such that the antenna arrangement sequentially is used in its different configuration states in order to identify the best suitable configuration state for communicating with another implantable medical device.

In one embodiment, at least one of the first implantable medical device and the second implantable medical device is a cardiac stimulation device, such as a pacemaker device or a cardioverter defibrillator.

In one embodiment, at least one of the first implantable medical device and the second implantable medical device is a leadless cardiac stimulation device, that is a cardiac stimulation device not comprising leads carrying electrodes. A leadless cardiac stimulation device of this kind may in particular be implanted directly into the patient's heart, for example the right ventricle or the right atrium.

Generally, one or multiple implantable medical devices of the intra-body network system may be implanted subcutaneously into a patient or directly into the patient's heart. For example, in one embodiment, one implantable medical device is implanted into the right ventricle and another implantable medical device is implanted into the right atrium of the patient's heart, a communication being established in between the intra-cardiac implantable medical devices within the intra-body network system.

In one embodiment, at least one of the first implantable medical device and the second implantable medical device is a subcutaneous cardiac loop recorder or a bio-sensor for measuring the blood pressure.

Generally, within the intra-body network system implantable medical devices, e.g., in the shape of stimulation devices, sensing devices, recording devices or marking devices may communicate with one another making use of antenna arrangements having different configuration states.

In another aspect, a method for operating an intra-body network system comprises: using a first communication circuitry of a first implantable medical device and a second communication circuitry of a second implantable medical device for establishing, in an implanted state of the first implantable medical device and the second implantable medical device, a communication for transmitting a communication signal from at least one of the first implantable medical device to the second implantable medical device and from the second implantable medical device to the first implantable medical device; and at least one of transmitting and receiving a communication signal using an antenna arrangement of the at least one of the first implantable medical device and the second implantable medical device, the antenna arrangement being configured to in a first configuration state using a first directive radiation characteristic and in a second configuration state using a second directive radiation characteristic different from the first directive radiation characteristic.

Additionally or alternatively, the antenna arrangement is configured to in a first configuration state using a first directive radiation characteristic, in a second configuration state using a second directive radiation characteristic different from the first directive radiation characteristic and in a third configuration state using a third directive radiation characteristic different from the first and the second directive radiation characteristic.

The advantages and advantageous embodiments described above for the intra-body network system equally apply also to the method, such that it shall be referred to the above in this respect.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein.

DETAILED DESCRIPTION

Figure 1:
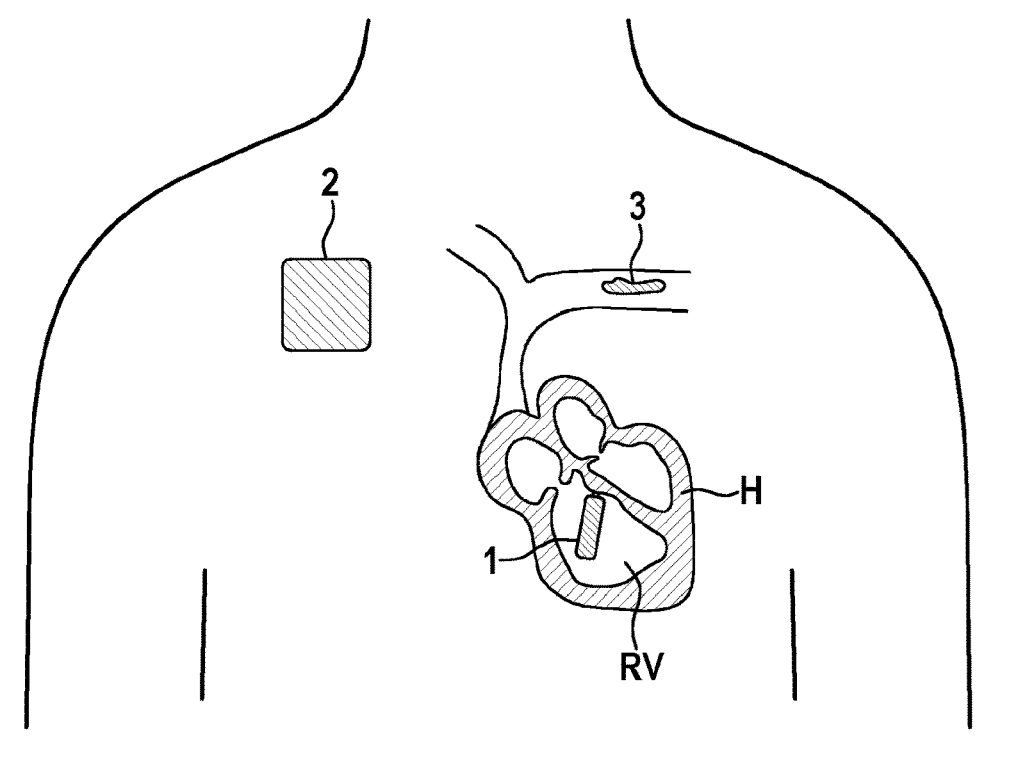
FIG. 1 shows a schematic drawing of an intra-body network system of medical devices implanted in a patient.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

Referring to FIG. 1, implantable medical devices 1, 2, 3 may be implanted in a patient at different locations in order to provide different functions within the patient. For example, a first implantable medical device 1 in the shape of a leadless pacemaker device may be implanted in the right ventricle RV of the patient's heart in order to provide for a pacing action within the heart H. Another or second implantable medical device 2 for example in the shape of a loop recorder may subcutaneously be implanted within the chest, the loop recorder allowing for a recording of signals and, for example, a communication with an external device in order to monitor certain parameters within the patient. Another or third implantable medical device 3 in the shape of a sensor device, for example a pressure sensor, a flow sensor or a temperature sensor or the like, may be implanted for example in a blood vessel in order to sense characteristic parameters such as a blood pressure or a blood flow.

There generally exists a desire for a data communication in between different medical devices 1, 2, 3 implanted in a patient. Approaches exist to establish a communication of this kind in a wireless fashion by establishing an intra-body network linking the medical devices 1, 2, 3 together, such that data may be exchanged in between the medical devices 1, 2, 3. A loop recorder may hence for example record sensor data of a sensor device, or data of a pacemaker or a cardioverter defibrillator, and may also provide data for example to a pacemaker or a cardioverter defibrillator to control a therapeutic action.

In order to allow for a data communication, a communication link between medical devices 1, 2, 3 needs to be established. Signals herein are exchanged in a modulated fashion making use of a particular transmission technology, such as an acoustic, radio frequency (RF), modulated electric field or magnetic (inductive) signal transmission, and a particular modulation scheme, such as a PCM, FSK, PSK, QPSK, FM, or AM modulation or the like. Regardless of the specific transmission technology, transmission generally takes place by employing a carrier frequency, which must match in between the communicating medical devices 1, 2, 3 in order to establish a reliable communication link.

Figure 2:
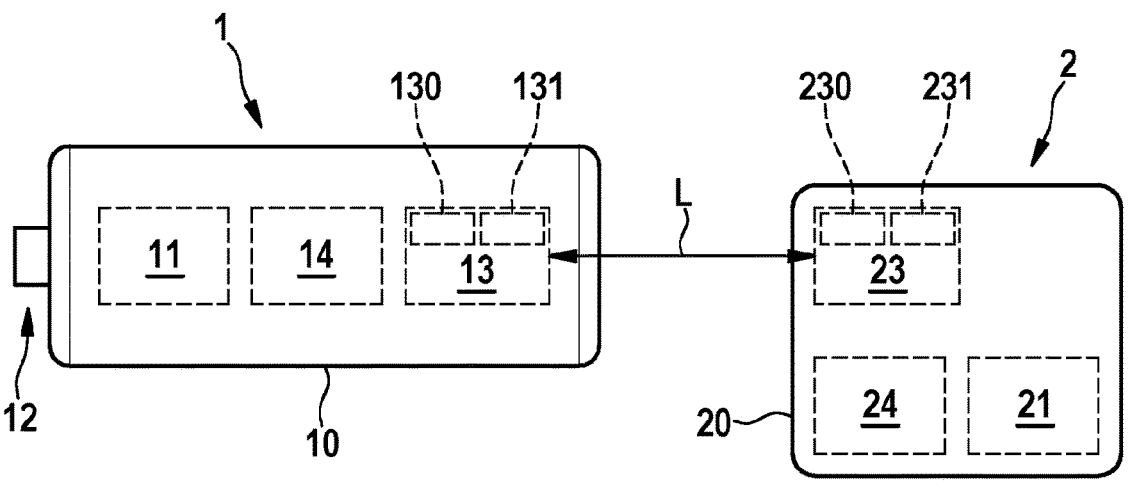
FIG. 2 shows a schematic drawing of two medical devices in between which a communication link for a data communication in between the medical devices shall be established.

Referring now to FIG. 2, medical devices 1, 2 to be implanted in a patient may have a small built and may be designed for a low power consumption in order to remain in a patient over a long-term.

A first medical device 1, for example in the shape of a leadless pacemaker, may herein comprise a housing 10, a control circuitry 11, an electrode arrangement 12 for emitting stimulation signals or receiving sense signals, a first communication circuitry 13 and an energy storage 14, for example in the shape of a battery.

A second medical device 2, for example in the shape of an implantable sensor device, such as a pressure sensor, or in the shape of a loop recorder, comprises a housing 20, a control circuitry 21, a second communication circuitry 23, and an energy storage 24, for example in the shape of a battery.

The communication circuitry 13, 23, in each case, comprises a transmission unit 130, 230, and a reception unit 131, 231. The communication circuitry 13, 23, is designed for the specific transmission technology, that is for transmitting and receiving of acoustic, radio frequency (RF), modulated electric field or magnetic signals. Also, the communication circuitry 13, 23 is designed to modulate respectively demodulate signals for transmission and reception, to optimize transmission parameters, to amplify received signals and to process signals in order to forward processed signals to the control circuitry 11, 21 for an analysis and control of the operation of the medical device 1, 2.

Generally, within an intra-body network system as schematically shown in FIG. 1, a communication in between implantable medical devices 1, 2, 3 shall be established using communication links. Referring for example to FIG. 2, a communication link L shall be established in between the medical devices 1, 2 for example at the initial startup of one of the medical devices 1, 2 or after exiting a sleep mode after a prolonged duration of passivity of the medical device 1, 2. Herein, a medical device 1, 2 which wishes to establish a communication may for example send out a trigger signal towards the other medical device 2, 1, the trigger signal indicating that the medical device 1 wishes to establish communication.

In order to allow for a communication in between implantable medical devices 1, 2, 3 of the intra-body network system, it is required that signals transmitted from one implantable medical device 1, 2, 3 may be received by another implantable medical device 1, 2, 3 with sufficient signal quality. For this, signals generally may be transmitted by one implantable medical device using an antenna having a substantially omnidirective radiation pattern, hence transmitting signals in all directions alike. Likewise, another implantable medical device may have an antenna having an omnidirective radiation pattern for omnidirectionally receiving signals. However, as there is a desire for transmitting and receiving signals in a directional manner in order to reduce energy consumption, within the instant text it is proposed to use implantable medical devices 1, 2, 3 having antenna arrangements exhibiting a directive radiation characteristic, such that a directional communication may be established in between pairs of implantable medical devices 1, 2, 3.

Figure 3:
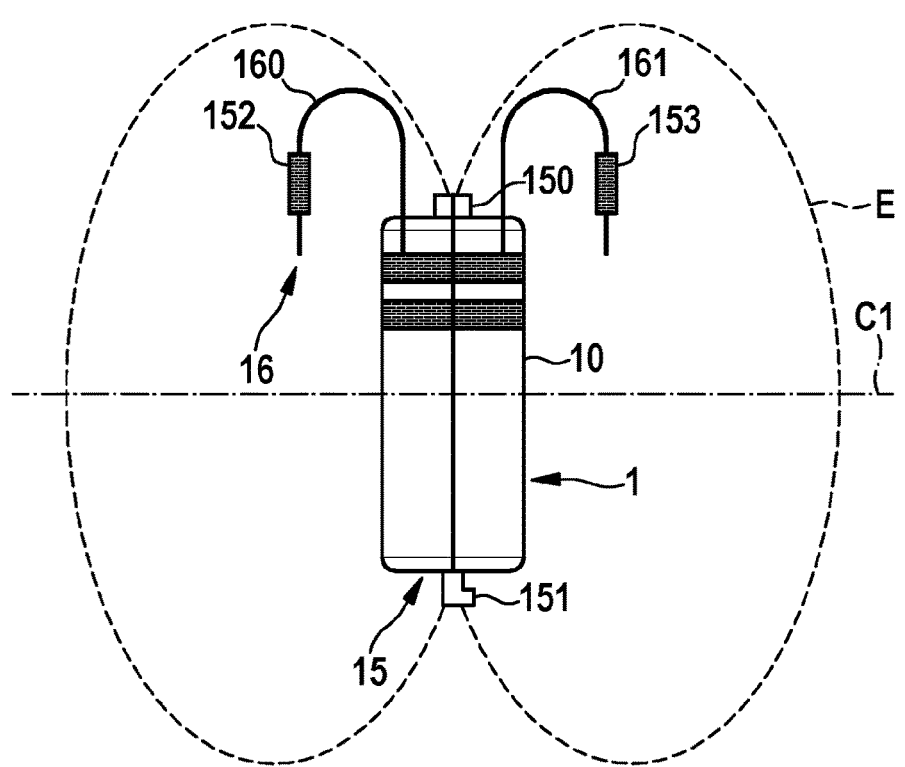
FIG. 3 shows a schematic drawing of an implantable medical device in the shape of a leadless pacemaker device having an antenna arrangement for communicating with another implantable medical device, in a first communication state of the antenna arrangement.
Figure 4:
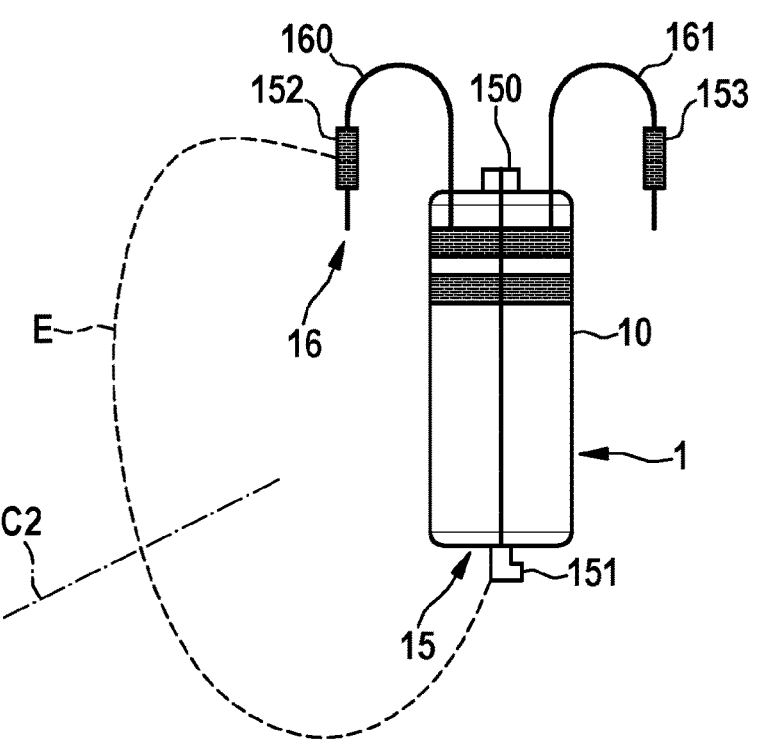
FIG. 4 shows a schematic drawing of the implantable medical device of FIG. 3, in a second communication state of the antenna arrangement.
Figure 5:
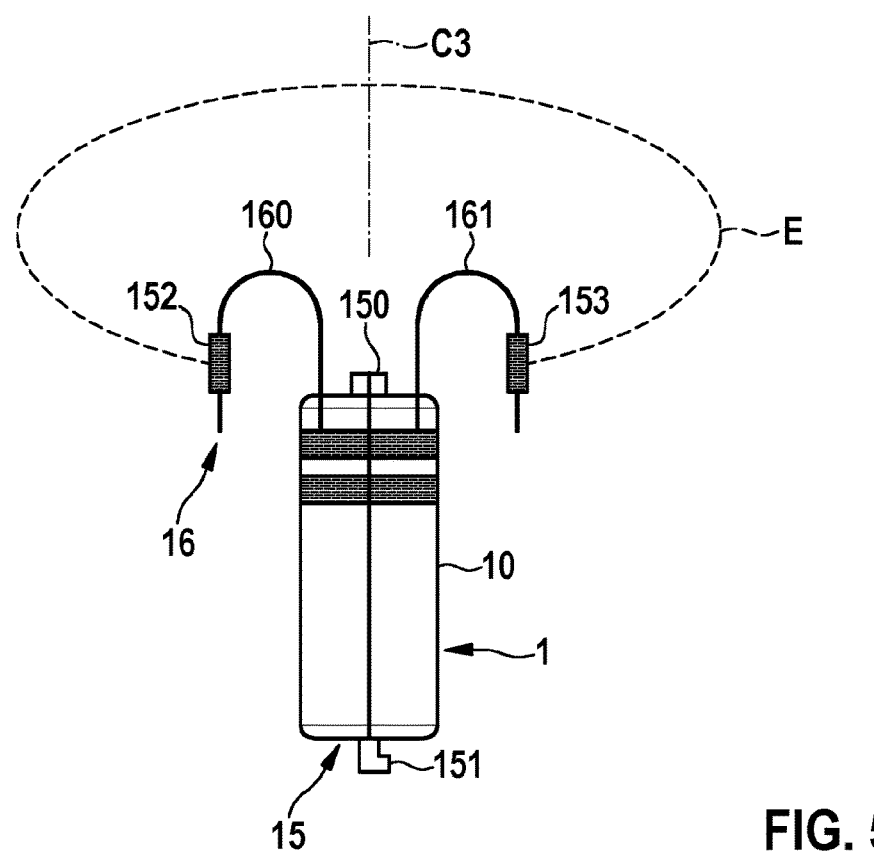
FIG. 5 shows a schematic drawing of the implantable medical device, in a third state of the antenna arrangement.

Referring now to FIGS. 3 to 5, in one embodiment an implantable medical device 1 may comprise an antenna arrangement 15 having antenna elements 152, 153 physically placed at different locations on the implantable medical device 1.

For example, a first antenna element may be formed by an electrode at a distal end of a housing 10 of the implantable medical device serving as a sensing electrode for sensing intra-cardiac signals. Another antenna element 151 may be formed by an electrode at an opposite, proximal end of the housing 10. Yet another antenna element 152 may be placed on a fixation element 160 of a fixation arrangement 16 for fixing the implantable medical device 1 to tissue in an implanted state. Yet another antenna element 153 may be placed on another fixation element 161 of the fixation arrangement 16.

The fixation elements 160, 161 may for example be formed by bendable tines, such as tines made from a shape memory alloy, for example nitinol. The antenna elements 152, 153 herein may be formed by the fixation elements 160, 161 as a whole, which for this purpose may be made from an electrically conductive material. In another embodiment, one or multiple antenna elements 152, 153, e.g., in the shape of electrodes may be placed on each fixation element 160, 161 in an electrically insulated fashion, such that the antenna elements 152, 153 of one fixation element 160, 161 may be operated substantially independent of one another.

For communicating with another implantable medical device 2, 3 different pairs of antenna elements 152, 153 may be used in order to establish different configuration states having different directional communication characteristics for, in the instant embodiment, transmitting or receiving a predominantly electric field E, as shown in FIGS. 3 to 5.

For example, in the configuration state of FIG. 3, antenna elements 150, 151 are used for transmitting and/or receiving signals E, the antenna arrangement 15 in this configuration state exhibiting a directive radiation characteristic with a predominant radiation along a communication plane C1.

This means that within the communication plane C1 the signal amplitude is largest on transmission, and sensitivity is largest upon reception.

In the shown embodiment, the directive radiation characteristic in the configuration state of FIG. 3 herein may be a rotationally symmetric, such that within the communication plane C1, as indicated in FIG. 3, an omnidirectional transmission and reception may be obtained.

In another configuration state, as indicated in FIG. 4, the antenna element 151 on the proximal end of the housing 10 and the antenna element 152 on the fixation element 160 of the fixation arrangement 16 in combination are used for communication. In this configuration state signals are transmitted and/or received along a communication plane C2, wherein in the communication plane C2 a particular directivity may be obtained achieving a directional transmission towards and/or reception from the side towards which the fixation element 160 extends from the housing 10, as illustrated in FIG. 4.

In another configuration state, the antenna element 151 at the proximal end of the housing 10 and the antenna element 153 of the fixation element 161 may be used for transmission and/or reception.

In yet another configuration state, the antenna elements 152, 153 placed on the fixation elements 160, 161 may be used for transmission and/or reception, in order to obtain a directive radiation characteristic for a predominant transmission and/or reception along a communication plane C3.

In yet another configuration state, more than two antenna elements 150 to 153 may be used in combination for transmitting and/or receiving signals.

For communicating with a particular one of the other implantable medical devices 2, 3, one of the configuration states may be chosen, in particular that configuration state which allows for a directive signal transmission towards or reception from the particular other implantable medical device 2, 3. The selection of the configuration state may take place in an initialization phase, during which the implantable medical device 1 may scan through the available configuration states and may identify that configuration state which allows for a most efficient communication. Once the most suitable configuration state is identified, that configuration state is selected for further communication with the particular implantable medical device 2, 3, such that in later operation a communication may be established using the selected configuration state.

If during operation it is detected that the communication quality deteriorates, the initialization phase may be started anew in order to identify the best suitable configuration state anew, in order to for example adjust for a displacement of an implantable medical device 1, 2, 3 within the patient.

In the embodiment of FIGS. 3 to 5 the antenna elements 150 to 153 may have the shape of electrodes for predominantly transmitting and receiving electrical signals E.

Figure 6:
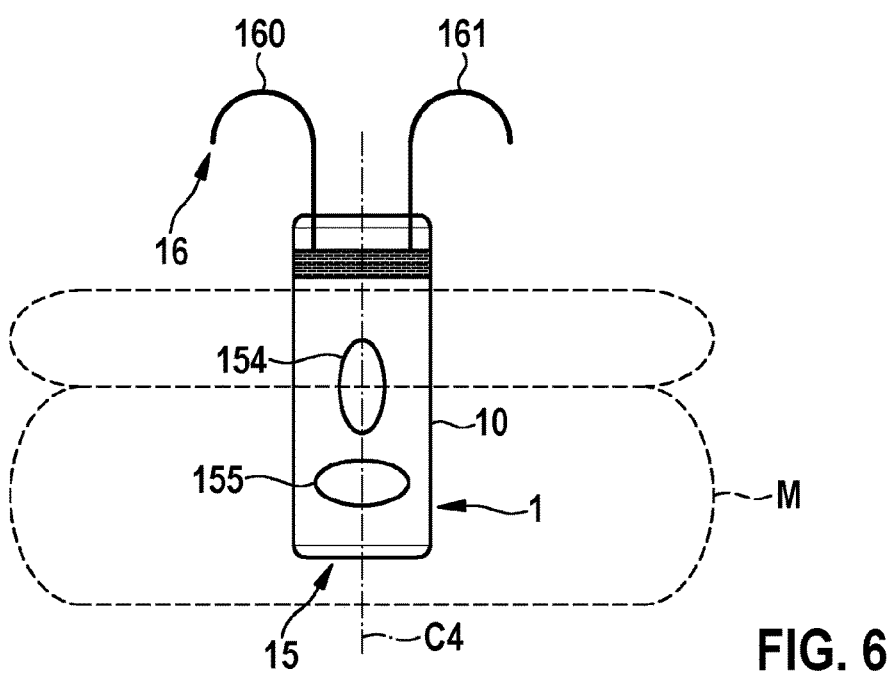
FIG. 6 shows a schematic drawing of another embodiment of an implantable medical device in the shape of a leadless pacemaker device having an antenna arrangement, in a first configuration state of the antenna arrangement.
Figure 7:
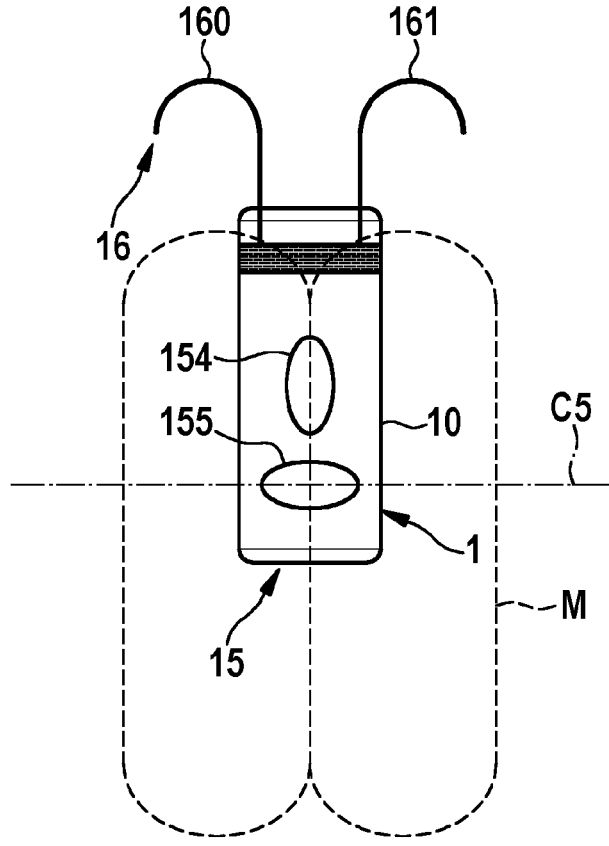
FIG. 7 shows a schematic drawing of the implantable medical device of FIG. 6, in a second configuration state of the antenna arrangement.

Referring now to FIGS. 6 and 7, in another embodiment the implantable medical device 1 may comprise antenna elements 154, 155 in the shape of magnetic coils, which each may for example be formed by a coil element formed by a wound wire or by a coil element formed on a printed circuit board. The antenna elements 154, 155 may be placed within the housing 10 and are configured to transmit and/or receive predominantly magnetic signals creating a predominantly magnetic field M.

Herein, the antenna elements 154, 155 are arranged such that in a first configuration state (FIG. 6) a signal transmission and/or reception is established predominantly along a communication plane C4 using the antenna element 154, whereas in a second configuration state (FIG. 7) a signal transmission and/or reception is established predominantly along a perpendicular communication plane C5 using the antenna element 155. An obtained radiation pattern herein may in each case be rotationally symmetric.

Using the different configuration states in the embodiment of FIGS. 6 and 7, a communication may be established to another implantable medical device 2, 3, wherein the best suitable configuration state may for example be chosen in an initial initialization phase, as it has been described before.

The implantable medical devices 1, 2, 3 within the intra-body network system may for example be cardiac stimulation devices, such as a leadless pacemaker devices or cardioverter defibrillators, sensing devices such as biosensors for example for sensing a blood pressure, or recording devices such as a loop recorder.

Generally, the implantable medical devices 1, 2, 3 may be implanted fully or in part directly into the patient's heart, for example the right ventricle or the right atrium. In another embodiment, the implantable medical devices 1, 2, 3 may be implanted fully or in part subcutaneously within the patient.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1, 2, 3 Implantable medical device
10, 20 Housing
11, 21 Control circuitry
12 Electrode arrangement
13, 23 Communication circuitry
130, 230 Transmission unit
131, 231 Reception unit
14, 24 Energy storage
15 Antenna arrangement
150-155 Antenna element
16 Fixation arrangement
160, 161 Fixation element
C1-C5 Communication plane
E Predominantly electric field
H Heart
L Communication link
M Predominantly magnetic field
RV Right ventricle

The invention claimed is:

1. An intra-body network system, comprising:
a first implantable medical device comprising a first communication circuitry; and
a second implantable medical device comprising a second communication circuitry;
wherein the first communication circuitry and the second communication circuitry are configured to establish, in an implanted state of the first implantable medical device and the second implantable medical device, a communication for transmitting a communication signal from at least one of the first implantable medical device to the second implantable medical device and from the second implantable medical device to the first implantable medical device;
wherein at least one of the first implantable medical device and the second implantable medical device comprises an antenna arrangement configured to at least one of transmit and receive a communication signal in a first configuration state using a first directive radiation characteristic, in a second configuration state using a second directive radiation characteristic different from the first directive radiation characteristic and a third configuration state using a third directive radiation characteristic different from the first directive radiation characteristic and the second directive radiation characteristic; and
wherein at least one of the first communication circuitry and the second communication circuitry is configured, in an initialization phase, to at least one of transmit and receive a communication signal using the first configuration state, the second configuration state and the third configuration state of the antenna arrangement in order to select a configuration state out of the first configuration state, the second configuration state and the third configuration state and, in an operational state, to use the selected configuration state for communication.

2. The intra-body network system according to claim 1, wherein the antenna arrangement is configured to at least one of transmit and receive a communication signal in said first configuration state predominantly along a first communication plane, in said second configuration state predominantly along a second communication plane and in said third configuration state predominantly along a third communication plane.

3. The intra-body network system according to claim 2, wherein the first communication plane and the second communication plane are oriented perpendicularly with respect to each other.

4. The intra-body network system according to claim 1, wherein the antenna arrangement comprises at least three antenna elements, wherein the antenna arrangement is configured to use a first set of the at least three antenna elements in the first configuration state, a second set of the at least three antenna elements in the second configuration state and a third set of the at least three antenna elements in the third configuration state.

5. The intra-body network system according to claim 4, wherein at least one of the at least three antenna elements is formed by an electrode for emitting or receiving electrical signals.

6. The intra-body network system according to claim 5, wherein the electrode is formed by a sensing electrode for sensing intra-cardiac signals.

7. The intra-body network system according to claim 4, wherein at least one of the at least three antenna elements is formed by a coil for emitting or receiving magnetic signals.

8. The intra-body network system according to claim 4, wherein said at least one of the first implantable medical device and the second implantable medical device comprises a housing, wherein at least one of the at least three antenna elements is placed on the housing.

9. The intra-body network system according to claim 4, wherein said at least one of the first implantable medical device and the second implantable medical device comprises a fixation arrangement comprising at least one fixation element for establishing a fixation to tissue, wherein at least one of the at least three antenna elements is placed on the at least one fixation element.

10. The intra-body network system according to claim 1, wherein the at least one of the first communication circuitry and the second communication circuitry is configured, in the initialization phase, to at least one of transmit and receive a communication signal by sequentially using the first configuration state, the second configuration state and the third configuration state of the antenna arrangement in order to select a configuration state out of the first configuration state, the second configuration state and the third configuration state.

11. The intra-body network system according to claim 1, wherein at least one of the first implantable medical device and the second implantable medical device is a cardiac stimulation device.

12. The intra-body network system according to claim 1, wherein at least one of the first implantable medical device and the second implantable medical device is a leadless cardiac stimulation device.

13. The intra-body network system according to claim 1, wherein at least one of the first implantable medical device and the second implantable medical device is a sub-cutaneous cardiac loop recorder or a bio-sensor for measuring the blood pressure.

14. A method for operating an intra-body network system, comprising:

using a first communication circuitry of a first implantable medical device and a second communication circuitry of a second implantable medical device for establishing, in an implanted state of the first implantable medical device and the second implantable medical device, a communication for transmitting a communication signal from at least one of the first implantable medical device to the second implantable medical device and from the second implantable medical device to the first implantable medical device; and at least one of transmitting and receiving a communication signal using an antenna arrangement of at least one of the first implantable medical device and the second implantable medical device, the antenna arrangement being configured to in a first configuration state using a first directive radiation characteristic, in a second configuration state using a second directive radiation characteristic different from the first directive radiation characteristic and in a third configuration state using a third directive radiation characteristic different from the first and the second directive radiation characteristic;

wherein at least one of the first communication circuitry and the second communication circuitry is configured, in an initialization phase, to at least one of transmit and receive a communication signal using the first configuration state, the second configuration state and the third configuration state of the antenna arrangement in order to select a configuration state out of the first configuration state, the second configuration state and the third configuration state and, in an operational state, to use the selected configuration state for communication.

*  *  *  *  *